US008647652B2

(12) United States Patent
Sharma

(10) Patent No.: US 8,647,652 B2
(45) Date of Patent: Feb. 11, 2014

(54) STABLE SILVER COLLOIDS AND SILICA-COATED SILVER COLLOIDS, AND METHODS OF PREPARING STABLE SILVER COLLOIDS AND SILICA-COATED SILVER COLLOIDS

(75) Inventor: Pramod K Sharma, Ann Arbor, MI (US)

(73) Assignee: Guardian Industries Corp., Auburn Hills, MI (US)

( * ) Notice: Subject to any disclaimer, the term of this patent is extended or adjusted under 35 U.S.C. 154(b) by 780 days.

(21) Appl. No.: 12/207,076

(22) Filed: Sep. 9, 2008

(65) Prior Publication Data

US 2010/0062033 A1    Mar. 11, 2010

(51) Int. Cl.
*A01N 25/34* (2006.01)

(52) U.S. Cl.
USPC ........... 424/411; 424/400; 424/405; 424/409; 424/417; 424/421; 424/618

(58) Field of Classification Search
None
See application file for complete search history.

(56) References Cited

U.S. PATENT DOCUMENTS

| | | |
|---|---|---|
| 3,573,470 A | 4/1971 | Haley |
| 4,504,888 A | 3/1985 | Rosenthal |
| 5,196,088 A | 3/1993 | Soda |
| 5,332,618 A | 7/1994 | Austin |
| 5,854,169 A | 12/1998 | Heller et al. |
| 5,912,045 A | 6/1999 | Eisenhammer et al. |
| 5,950,106 A | 9/1999 | May et al. |
| 5,981,425 A | 11/1999 | Hiroshi et al. |
| 6,013,372 A | 1/2000 | Hayakawa et al. |
| 6,054,227 A | 4/2000 | Greenberg et al. |
| 6,071,606 A | 6/2000 | Yamakazi et al. |
| 6,103,363 A | 8/2000 | Boire et al. |
| 6,277,169 B1 | 8/2001 | Hampden-Smith et al. |
| 6,284,377 B1 | 9/2001 | Veerasamy |
| 6,344,242 B1 | 2/2002 | Stolk et al. |
| 6,362,121 B1 | 3/2002 | Chopin et al. |
| 6,420,437 B1 | 7/2002 | Mori et al. |
| 6,679,978 B2 | 1/2004 | Johnson et al. |
| 7,049,002 B2 | 5/2006 | Greenberg et al. |
| 7,144,840 B2 | 12/2006 | Yeung et al. |
| 7,473,369 B2 | 1/2009 | Meng et al. |

(Continued)

FOREIGN PATENT DOCUMENTS

| | | |
|---|---|---|
| EP | 0 818 561 A1 | 1/1998 |
| EP | 1 205 243 A1 | 5/2002 |

(Continued)

OTHER PUBLICATIONS

J. Nelson et al., "Photoconductivity and charge trapping in porous nanocrystalline titanium dioxide," *Journal of Photochemistry and Photobiology A: Chemistry*, 148 (2002) 25-31.

(Continued)

*Primary Examiner* — Robert A Wax
*Assistant Examiner* — Danah Al-Awadi
(74) *Attorney, Agent, or Firm* — O'Brien Jones PLLC

(57) ABSTRACT

Methods for preparing silver colloids and silica-coated silver colloids are disclosed. The silver colloids may be prepared by heating a silver-containing solution, combining the heated silver-containing solution with an acid solution, and cooling the combined solutions to form a silver colloid containing silver particles. The silver particles in the silver colloid can further be coated with silica. A method for preparing antimicrobial coatings is also disclosed.

10 Claims, 6 Drawing Sheets

(56) References Cited

U.S. PATENT DOCUMENTS

| | | | |
|---|---|---|---|
| 7,605,186 | B2 | 10/2009 | Chung et al. |
| 7,846,866 | B2 | 12/2010 | Sharma |
| 8,197,884 | B2 | 6/2012 | Es-Souni |
| 2002/0030188 | A1 | 3/2002 | Hayashi et al. |
| 2002/0150681 | A1 | 10/2002 | Boire et al. |
| 2003/0039843 | A1 | 2/2003 | Johnson et al. |
| 2003/0143437 | A1 | 7/2003 | Ohtsu et al. |
| 2003/0235695 | A1 | 12/2003 | Greenberg et al. |
| 2004/0067849 | A1 | 4/2004 | Tanaka et al. |
| 2006/0019028 | A1 | 1/2006 | Yeung et al. |
| 2006/0091079 | A1 | 5/2006 | Meng et al. |
| 2007/0017567 | A1 | 1/2007 | Gronet et al. |
| 2007/0099003 | A1 | 5/2007 | Lee et al. |
| 2007/0146889 | A1 | 6/2007 | Wang et al. |
| 2007/0151482 | A1 | 7/2007 | Im et al. |
| 2008/0020127 | A1 | 1/2008 | Whiteford et al. |
| 2008/0145625 | A1 | 6/2008 | Schumacher et al. |
| 2008/0302448 | A1* | 12/2008 | Frey et al. ............. 148/274 |
| 2009/0061230 | A1 | 3/2009 | Berkei et al. |
| 2009/0075069 | A1 | 3/2009 | Myli et al. |
| 2009/0214766 | A1* | 8/2009 | Magdassi et al. ........ 427/125 |
| 2009/0286676 | A1 | 11/2009 | Kim et al. |
| 2011/0045970 | A1 | 2/2011 | Sharma et al. |
| 2011/0076450 | A1 | 3/2011 | Sharma et al. |

FOREIGN PATENT DOCUMENTS

| | | | |
|---|---|---|---|
| EP | 1 316 532 | A1 | 6/2003 |
| GB | 2 208 874 | A | 4/1989 |
| JP | 08-099041 | A | 4/1996 |
| JP | 08-196903 | A | 8/1996 |
| JP | 11-228865 | A | 8/1999 |
| JP | 2001-286766 | | 10/2001 |
| JP | 2004-001400 | | 1/2004 |
| JP | 2004-092163 | A | 3/2004 |
| JP | 2006-198466 | A | 8/2006 |
| KR | 10-2004-0024582 | A | 3/2004 |
| KR | 10-0421243 | B1 | 3/2004 |
| KR | 10-0541750 | B1 | 1/2006 |
| KR | 10-0727579 | B1 | 6/2007 |
| KR | 10-0753055 | B1 | 8/2007 |
| KR | 10-2008-0030981 | A | 4/2008 |
| WO | 97/24471 | A1 | 7/1997 |
| WO | WO 02/06159 | A1 | 1/2002 |
| WO | WO 03/009061 | A2 | 1/2003 |
| WO | WO 2005/105332 | | 11/2005 |
| WO | 2007/107792 | A1 | 9/2007 |
| WO | WO 2007/107792 | * | 10/2007 |
| WO | WO 2007/117332 | A2 | 10/2007 |
| WO | WO 2007/147399 | A2 | 12/2007 |
| WO | WO 2010/028109 | A1 | 3/2010 |
| WO | WO 2010/030550 | A3 | 3/2010 |
| WO | WO 2010/030551 | A1 | 3/2010 |
| WO | WO 2010/030552 | | 3/2010 |
| WO | WO 2010/062433 | | 6/2010 |
| WO | WO 2011/041218 | | 4/2011 |

OTHER PUBLICATIONS

T. Watanabe et al., "Photocatalytic activity and photoinduced hydrophilicity of titanium dioxide coated glass," *Thin Solid Films*, 351 (1999) 260-263.

N. Sakai et al., "Effect of Ultrasonic Treatment on Highly Hydrophilic $TiO_2$ Surfaces," *Langmuir*, 1998, 14, 5918-5920.

Y. C. Lee et al, "Photocatalysis and hydrophilicity of doped $TiO_2$ thin films," *Journal of Colloid and Interface Science*, 267, (2003) 127-131.

S. V. Manorama et al., "Photostabilization of dye on anatase titania nanoparticles by polymer capping," *Journal of Physics and Chemistry of Solids*, 63 (2002) 135-143.

A. Conde-Gallardo et al., "$TiO_2$ anatase thin films deposited by spray pyrolysis of an aerosol of titanium diisopropoxide," *Thin Solid Films*, 473 (2005) 68-73.

K.-H. Haas et al, "Functionalized coatings based on inorganic-organic polymers (ORMOCER® s) and their combination with vapor deposited inorganic thin films," *Surface and Coatings Technology*, 111 (1999) 72-79.

R. van Grieken et al., 'Synthesis of size-controlled silica-supported $TiO_2$ photocatalysts, *Journal of Photochemistry and Photobiology A: Chemistry*, 148 (2002) 315-322.

Co-pending U.S. Appl. No. 12/207,359, filed Sep. 9, 2008.
Co-pending U.S. Appl. No. 12/207,235, filed Sep. 9, 2008.
Co-pending U.S. Appl. No. 12/207,167, filed Sep. 9, 2008.
Co-pending U.S. Appl. No. 12/263,968, filed Nov. 3, 2008.
Co-pending U.S. Appl. No. 12/263,991, filed Nov. 3, 2008.

International Search Report in PCT/US2009/055827 having a mailing date of Apr. 20, 2010.

Written Opinion of the International Searching Authority in PCT/US2009/055827 having a mailing date of Apr. 20, 2010.

Jung et al., "Photoactivity of $SiO_2/TiO_2$ and $ZrO_2/TiO_2$ mixed oxides prepared by sol-gel method", Material Letters 58 (2004), pp. 2897-2900.

U.S. Office Action dated Mar. 14, 2012 from co-pending U.S. Appl. No. 12/569,177.

U.S. Office Action dated Apr. 18, 2012 from co-pending U.S. Appl. No. 12/207,235.

Russian Office Action dated Jun. 20, 2011 for Russian App. No. 2011113971/20.

English language translation of Saudi Arabia App. No. 07280093(1) mailed Feb. 17, 2012.

English language abstract of JP 07100378 A, 1993.

Russian Office Action dated Apr. 26, 2012 from co-pending RU Application No. 2011113541.

Canadian Office Action dated Apr. 19, 2012 from co-pending CA Application No. 2,735,861.

Russian Office Action dated Apr. 20, 2011 from co-pending RU Application No. 2011113971.

Imai et al., "Preparation of porous anatase coating from sol-gel derived titanium dioxide and titanium dioxide-silica by water-vapour exposure", Journal of American Ceramic Society, 82 [9], pp. 2301-2304, Jan. 1, 1999.

Aubry, E. et al., "Poisoning prevention of $TiO_2$ photocatalyst coatings sputtered on soda-lime glass by intercalation of SiNx diffusion barriers" Surface & Coatings Technology 201, 2007, pp. 7706-7712.

He, C. et al., "Influence of silver doping on the photocatalytic activity of titania films" Applied Surface Science 200, 2002, pp. 239-247.

Page, K et al., "Titania and silver-titania composite films on glass—potent antimicrobial coatings" Journals of Matierals Chemistry 17, 2007, pp. 95-104.

Seery, M. et al., "Silver doped titanium dioxide nanomaterials for enhanced visible light photocatalysis" Journal of Photochemistry and Photobiology 189, 2007, pp. 258-263.

European Search Report for European Application No. EP 09813467.9 dated Oct. 21, 2011.

International Search Report and Written Opinion for International Publication No. WO 2010/028109 (International Application No. PCT/US2009/055823) dated Mar. 11, 2010.

International Search Report and Written Opinion for International Publication No. WO 2010/030551 (International Application No. PCT/US2009/055826) dated Mar. 18, 2010.

International Search Report and Written Opinion for International Publication No. WO 2010/062433 (International Application No. PCT/US2009/055829) dated Mar. 10, 2010.

International Search Report and Written Opinion for International Publication No. WO 2010/030550 (International Application No. PCT/US2009/055824) dated Apr. 16, 2010.

International Search Report and Written Opinion for International Publication No. WO 2011/041218 (International Application No. PCT/US2010/050118) dated Jun. 23, 2011.

U.S. Office Action dated Apr. 15, 2009 from co-pending U.S. Appl. No. 12/207,359.

U.S. Office Action dated Sep. 30, 2009 from co-pending U.S. Appl. No. 12/207,359.

U.S. Notice of Allowance dated Apr. 12, 2010 from co-pending U.S. Appl. No. 12/207,359.

(56) References Cited

OTHER PUBLICATIONS

U.S. Notice of Allowance dated Jul. 29, 2010 from co-pending U.S. Appl. No. 12/207,359.
U.S. Office Action dated Apr. 9, 2009 from co-pending U.S. Appl. No. 12/207,235.
U.S. Office Action dated Nov. 12, 2009 from co-pending U.S. Appl. No. 12/207,235.
U.S. Office Action dated Apr. 12, 2010 from co-pending U.S. Appl. No. 12/207,235.
U.S. Office Action dated Dec. 3, 2010 from co-pending U.S. Appl. No. 12/207,235.
U.S. Office Action dated Jun. 16, 2011 from co-pending U.S. Appl. No. 12/207,235.
U.S. Office Action dated Oct. 5, 2011 from co-pending U.S. Appl. No. 12/207,235.
U.S. Office Action dated Jun. 17, 2011 from co-pending U.S. Appl. No. 12/207,167.
U.S. Office Action dated Nov. 21, 2011 from co-pending U.S. Appl. No. 12/207,167.
U.S. Office Action dated Feb. 17, 2011 from co-pending U.S. Appl. No. 12/263,968.
U.S. Office Action dated Sep. 2, 2011 from co-pending U.S. Appl. No. 12/263,968.
U.S. Office Action dated Apr. 20, 2011 from co-pending U.S. Appl. No. 12/263,991.
U.S. Office Action dated Oct. 11, 2011 from co-pending U.S. Appl. No. 12/263,991.
European Search Report for European Application No. EP 09813466.1 dated Feb. 6, 2012.
Goldberg, M.M., "Raw Materials and Intermediate Products for Paint Materials," from "Chemistry," Moscow, 1978, pp. 277-281.
Office Action, Russian Application 2011113970/05, dated Apr. 19, 2013.
Kuznesof, P.M. and Rao, M.V., "Titanium Dioxide—Chemical and Technical Assessment", *Titanium Dioxide* (CTA) 2006, pp. 1-8.
Nissan Chemical, Organosilicasol information sheet, 2007.
Office Action, U.S. Appl. No. 12/914,102 dated Jan. 17, 2013.
Office Action, U.S. Appl. No. 12/263,968 dated Dec. 20, 2012.
Office Action, U.S. Appl. No. 12/263,991 dated Feb. 4, 2013.
Office Action, U.S. Appl. No. 12/207,235 dated May 6, 2013.
Office Action, U.S. Appl. No. 12/263,991 dated May 21, 2013.
Notice of Allowance, U.S. Appl. No. 12/263,968 dated May 28, 2013.
Office Action, U.S. Appl. No. 12/914,102, dated May 23, 2013.
Office Action, U.S. Appl. No. 12/569,177 dated Aug. 1, 2013.
Machine Translation of KR 10-2008-0030981 A obtained from the EPO dated Oct. 16, 2012 (16 pages).
Advisory Action dated Nov. 30, 2012 from co-pending U.S. Appl. No. No. 12/569,177.
Advisory Action dated Feb. 16, 2012 from co-pending U.S. Appl. No. No. 12/263,968.
Office Action dated Dec. 20, 2012 from co-pending U.S. Appl. No. 12/263,968.
Advisory Action dated Jun. 27, 2012 from co-pending U.S. Appl. No. 12/207,235.
Office Action dated Aug. 22, 2012 from co-pending U.S. Appl. No. 12/207,235.
Office Action dated Jul. 16, 2012 from co-pending U.S. Appl. No. 12/569,177.
Response to Office Action dated Feb. 1, 2010 from co-pending U.S. Appl. No. 12/207,359.
Response to Office Action dated Apr. 23, 2012 from co-pending U.S. Appl. No. 12/207,167.
Response to Office Action dated Apr. 4, 2011 from co-pending U.S. Appl. No. 12/207,235.
Response to Office Action dated Feb. 6, 2012 from co-pending U.S. Appl. No. 12/207,235.
Response to Office Action dated Feb. 9, 2010 from co-pending U.S. Appl. No. 12/207,235.
Response to Office Action dated Jul. 8, 2009 from co-pending U.S. Appl. No. 12/207,235.
Response to Office Action dated Jun. 18, 2012 from co-pending U.S. Appl. No. 12/207,235.
Response to Office Action dated Dec. 8, 2009 from co-pending U.S. Appl. No. 12/207,359.
Response to Office Action dated Jul. 8, 2009 from co-pending U.S. Appl. No. 12/207,359.
Response to Office Action dated Feb. 2, 2012 from co-pending U.S. Appl. No. 12/263,968.
Response to Office Action dated Jun. 16, 2011 from co-pending U.S. Appl. No. 12/263,968.
Response to Office Action dated Mar. 1, 2012 from co-pending U.S. Appl. No. 12/263,968.
Response to Office Action dated Jun. 14, 2012 from co-pending U.S. Appl. No. 12/569,177.
Response to Office Action dated Mar. 12, 2012 from co-pending U.S. Appl. No. 12/263,991.
Response to Office Action dated Sep. 20, 2011 from co-pending U.S. Appl. No. 12/263,991.
Response to Office Action dated Nov. 16, 2012 from co-pending U.S. Appl. No. 12/569,177.
Response to Office Action dated Sep. 19, 2011 from co-pending U.S. Appl. No. 12/207,167.
Response to Office Action dated Sep. 28, 2010 from co-pending U.S. Appl. No. 12/207,235.
Response to Office Action dated Sep. 8, 2011 from co-pending U.S. Appl. No. 12/207,235.
English language Abstract for KR 20080026080.

\* cited by examiner

US 8,647,652 B2

STABLE SILVER COLLOIDS AND SILICA-COATED SILVER COLLOIDS, AND METHODS OF PREPARING STABLE SILVER COLLOIDS AND SILICA-COATED SILVER COLLOIDS

FIELD

The present invention relates generally to silver colloids, silica-coated silver colloids, and methods of preparing silver colloids and silica-coated silver colloids. The invention also relates to antimicrobial coatings on substrates using silver colloids and silica-coated silver colloids.

BACKGROUND

Colloidal silver is a natural antibiotic and preventative against infections. In the past, colloidal silver was administered by physicians as an antibiotic to kill infectious bacteria. While not wishing to be limited by the following theory, it is believed that silver may act as a catalyst to disable an enzyme that one-celled bacteria and fungi need for their oxygen metabolism, without interfering with human enzymes of bodily functions. Silver has also found use in coatings to provide antimicrobial properties.

Methods exist to produce silver colloids. Known chemical methods, however, produce low quality silver colloids that are highly unstable with time. The silver colloids prepared by these chemical methods settle out of solution quickly, e.g., in a matter of minutes.

One method that produces high grade silver colloids comprises a process that collides water and silver particles in an electric current so that the silver particles and water disperse around and bind to each other. This electro-colloidal process provides very fine silver particles suspended indefinitely in water. The electro-colloidal process, however, is expensive.

There is thus a long-felt need in the industry for a method of forming silver colloids by a process that may be cost-effective and may provide a silver colloid that is stable for longer periods of time.

SUMMARY

In accordance with various exemplary embodiments of the invention are provided methods for preparing silver colloids. The methods according to the present invention may form silver colloids that are stable over a long period of time.

Other exemplary embodiments of the invention relate to methods for preparing silica-coated silver colloids.

Other exemplary embodiments of the invention relate to methods for forming a coating containing silver on a substrate, such as an antimicrobial coating.

As described herein, the invention relates to methods for preparing silver colloids and silica-coated silver colloids, and the formation of silver-containing coatings using the silver colloids and silica-coated silver colloids. In the following description, certain aspects and embodiments will become evident. It should be understood that the invention, in its broadest sense, could be practiced without having one or more features of these aspects and embodiments. It should be understood that these aspects and embodiments are merely exemplary and explanatory, and are not restrictive of the invention as claimed.

BRIEF DESCRIPTION OF THE DRAWINGS

The following figures, which are described below and which are incorporated in and constitute a part of the specification, illustrate exemplary embodiments of the invention and are not to be considered limiting of the scope of the invention, for the invention may admit to other equally effective embodiments.

DESCRIPTION OF EXEMPLARY EMBODIMENTS

Figure 1:
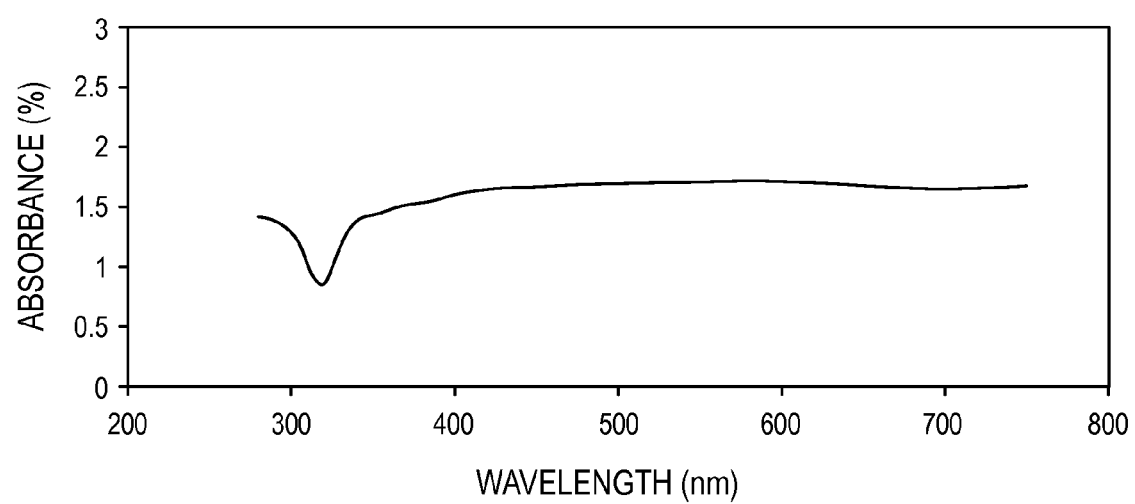
FIG. 1 is a UV absorption spectrum of the silver colloid of a Comparative Example.

Reference will now be made to various exemplary embodiments of the invention, examples of which are illustrated in the accompanying figures. However, these various exemplary embodiments are not intended to limit the disclosure, but rather numerous specific details are set forth in order to provide a thorough understanding of the invention. It will be apparent to one skilled in the art that the invention may be practiced without some or all of these specific details, and the disclosure is intended to cover alternatives, modifications, and equivalents. For example, well-known features and/or process steps may not have been described in detail so as not to unnecessarily obscure the invention. In addition, it is not contemplated that every embodiment of the invention will provide results and/or analytical data substantially as reported in the Examples and Figures herein. One of skill in the art, practicing the invention in light of the disclosure herein and with reference to information within the general knowledge of those skilled in the art, will appreciate the range of embodiments which can be practiced and remain within the scope of the invention.

The present invention contemplates various exemplary methods of preparing a silver colloid. In one exemplary embodiment, a method of preparing a silver colloid comprises heating a silver-containing solution, combining the heated silver-containing solution with an acid solution, and cooling the resulting solution to form a silver colloid. In one exemplary embodiment, the silver-containing solution may be heated to a boil. The resulting solution may optionally be cooled, for example by allowing the solution to slowly cool to room temperature.

Various methods in accordance with exemplary embodiments of the invention may improve the stability of the silver colloid, the size of the silver particles in the silver colloid, or both.

In at least one embodiment of the present invention, the silver-containing solution comprises an aqueous solution of a silver salt, such as, for example, silver nitrate.

In exemplary embodiments of the present invention, the acid solution may be chosen from, for example, sodium citrate, citric acid, malic acid, alkali-based acids, or other organic acids. In at least one embodiment, the acid solution comprises sodium citrate.

In one exemplary embodiment, the silver colloid comprises silver particles having a particle size that ranges from about 10 nm to about 200 nm. For example, in at least one embodiment, the particle size of the silver particles ranges from about 20 nm to about 150 nm.

In various exemplary embodiments, the silver colloid may be stable for at least about 24 hours, such as at least about 3 days, at least about 10 days, or at least about 15 days.

At least one embodiment of the present invention relates to a method of preparing a silica-coated silver colloid. For example, a silver colloid may be formed by heating a silver-containing solution, combining the heated silver-containing solution with an acid solution, and cooling the resulting solution, followed by adding aqueous ammonia and ethanol to the silver colloid, and then adding tetraethoxysilane (TEOS) and allowing the silver particles to be coated with silica. In at least one embodiment, the silica may comprise amorphous, or non-crystalline, silica.

In at least one embodiment, the silica-coated silver colloid comprises silica-coated silver particles having a particle size less than about 300 nm, such as silica-coated silver particles having a particle size that ranges from about 110 nm to about 300 nm. In at least one further embodiment, the particle size of the silica-coated silver particles ranges from about 120 nm to about 250 nm.

In at least one embodiment, the silica-coated silver colloid may be stable for at least about 24 hours, such as at least about 3 days or at least about 10 days.

In various exemplary embodiments of the present invention, methods of forming an antimicrobial coating containing silver are contemplated. In one exemplary method, a silver colloid may be formed by heating a silver-containing solution, combining the heated silver-containing solution with an acid solution, and cooling the resulting solution, followed by coating a substrate with the silver colloid and drying. In one exemplary method, the silver colloid solution is mixed with an aqueous ammonia/ethanol solution, and then with a tetraethoxysilane solution to coat the silver particles with silica prior to forming a coating on a substrate.

In at least one exemplary embodiment, the substrate comprises a glass substrate. For example, the glass substrate may be chosen from a standard clear glass or a low iron glass, such as ExtraClear™, UltraWhite™, or Solar glasses available from Guardian Industries. In one exemplary embodiment, coating a glass substrate with a coating according to the invention may allow for a relatively higher transmission of light.

The following examples are not intended to be restrictive of the invention as claimed, but rather, are merely intended to further illustrate various embodiments of the invention.

EXAMPLES

Comparative Example

A solution of 0.01 g silver nitrate in 100 g water was prepared. A separate solution of sodium citrate in water was prepared. The sodium citrate solution was added to the silver nitrate solution and stirred for 30 min. The color of the solution became bluish yellow. The UV spectrum of the silver colloid of the Comparative Example is shown in FIG. 1. The colloid was very unstable and silver particles settled after 10 minutes.

Example 1

Silver Colloid 250 g of water were heated to boiling. 50 mg of silver nitrate was added to the water. A separate solution of 1 g of sodium citrate in 100 g of water was prepared. 10 g of the sodium citrate solution was then added to the silver nitrate solution and stirred for 30 min. The resulting solution was allowed to cool down to room temperature. The silver colloid solution was greenish yellow, indicative of the presence of silver having good crystallinity.

Figure 2:
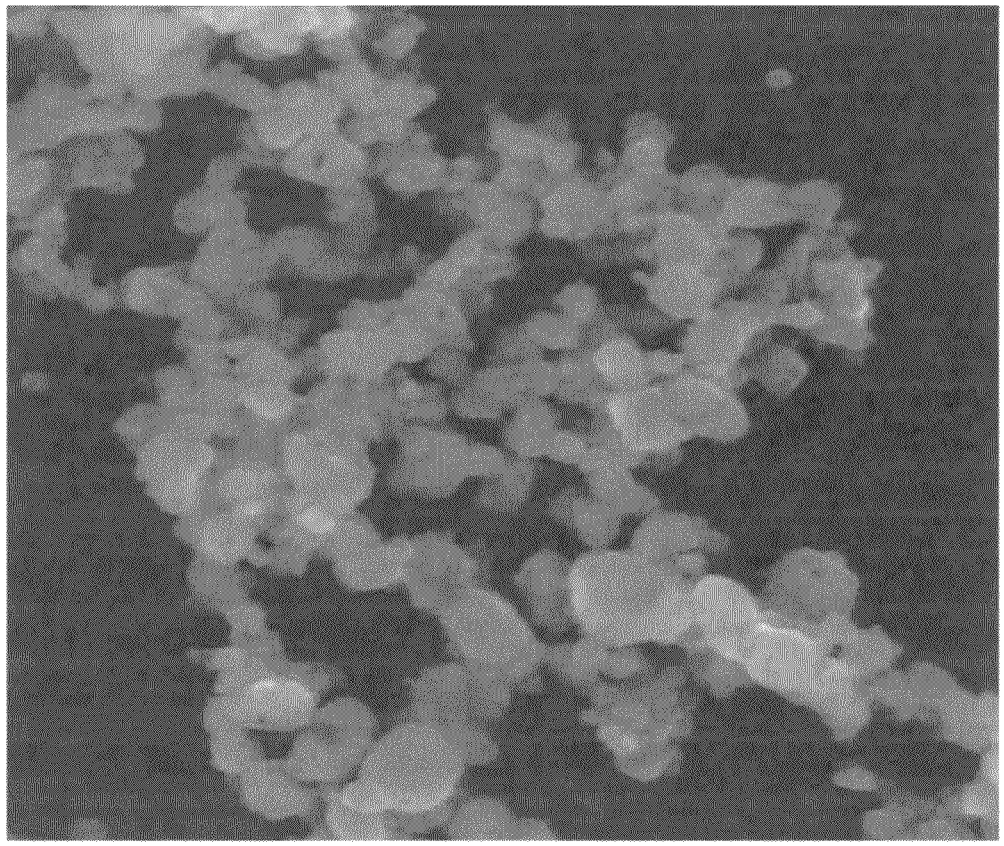
FIG. 2 is an SEM micrograph of a silver colloid of an exemplary embodiment of the present invention.
Figure 3:
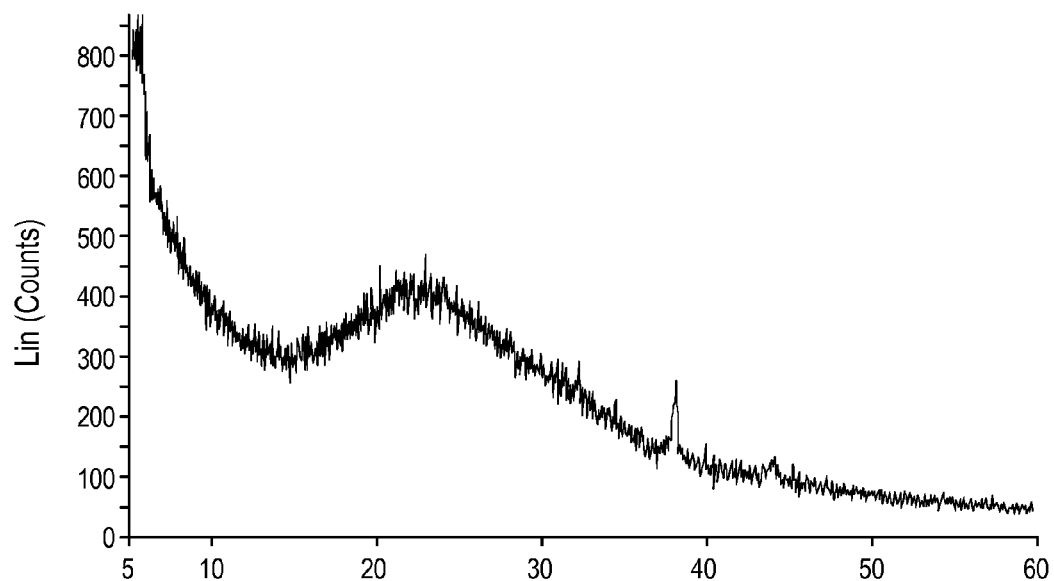
FIG. 3 is a x-ray diffraction pattern of a silver colloid according to an exemplary embodiment of the present invention.
Figure 4:
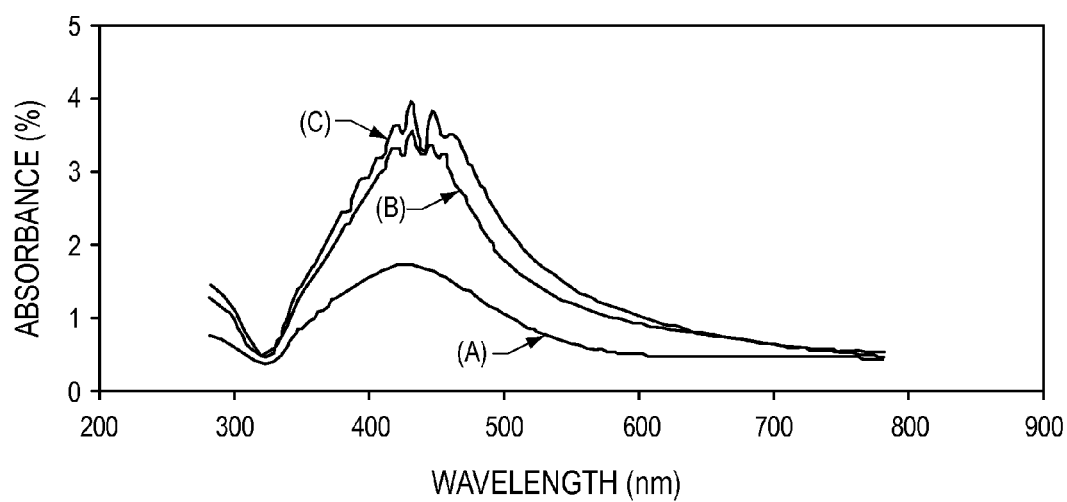
FIG. 4 is an absorption spectra of a silver colloid according to an exemplary embodiment of the present invention.

An SEM micrograph of the colloidal silver is shown in FIG. 2, indicating a particle size of 20 nm to 150 nm. The colloidal silver was then spin coated on a glass substrate and heated to 50° C. to dry the coating. FIG. 3 shows the x-ray diffraction (XRD) pattern of the colloidal silver, which indicates peaks at 38.12° and 44.34° corresponding to the (111) and (200) reflections of face centered cubic (fcc) phase of silver (JCPDS card no. 4-783), respectively. The absorption spectra of the colloidal silver is shown in FIG. 4, which indicates an absorbance peak at 425 nm, which is a typical peak of silver metal that appears in the visible spectra.

The silver colloid was very stable and did not show any settlement of particles after 15 days. FIG. 4 shows the absorption spectra of the colloidal silver after aging (A) 1 day, (B) 10 days, and (C) 12 days. The increase in absorbance indicates that the size of the silver particles increased over time.

Example 2

Silica-Coated Silver Colloid

A solution containing 100 ml of ethanol and 0.5 ml of $NH_4OH$ was prepared. 20 ml of the silver colloid as prepared in Example 1 above was added to an empty 100 ml bottle. 2 ml of the $NH_4OH$/ethanol solution was added to the silver colloid solution and mixed for 5 minutes. 0.2 ml of tetraethoxysilane (TEOS) was added to the solution containing silver colloid and $NH_4OH$/ethanol and stirred vigorously. The solution was stored overnight without shaking or disturbing. The solution was then spin coated on a glass substrate and dried at 50° C.

Figure 5:
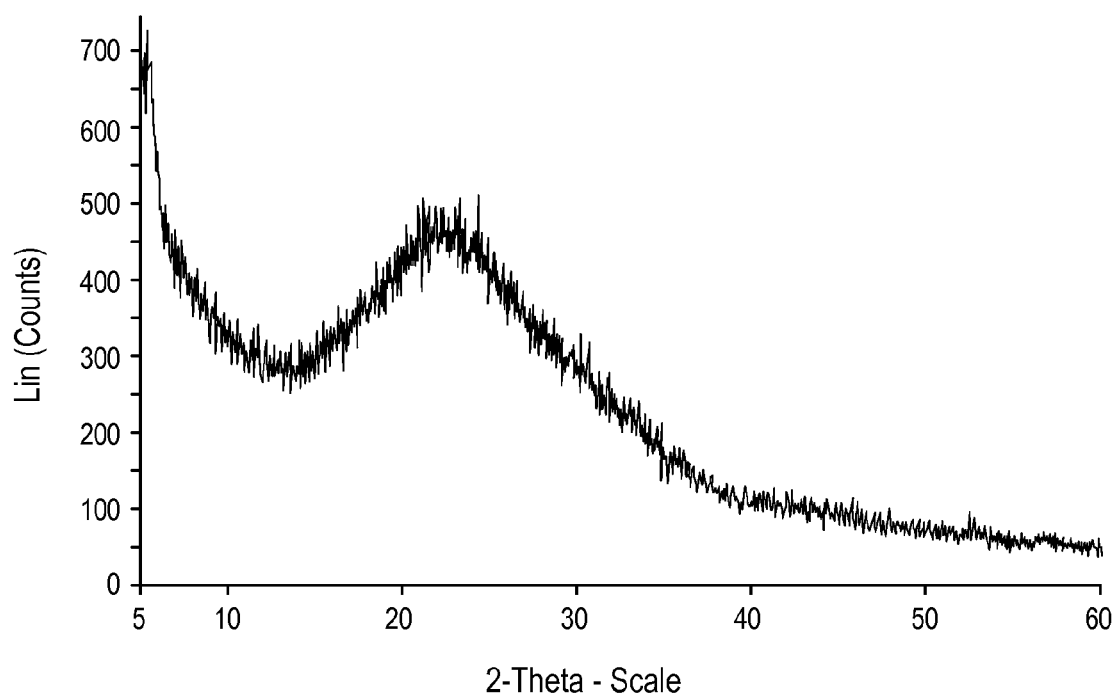
FIG. 5 is an x-ray diffraction pattern of a silica-coated silver colloid according to an exemplary embodiment of the present invention.
Figure 6:
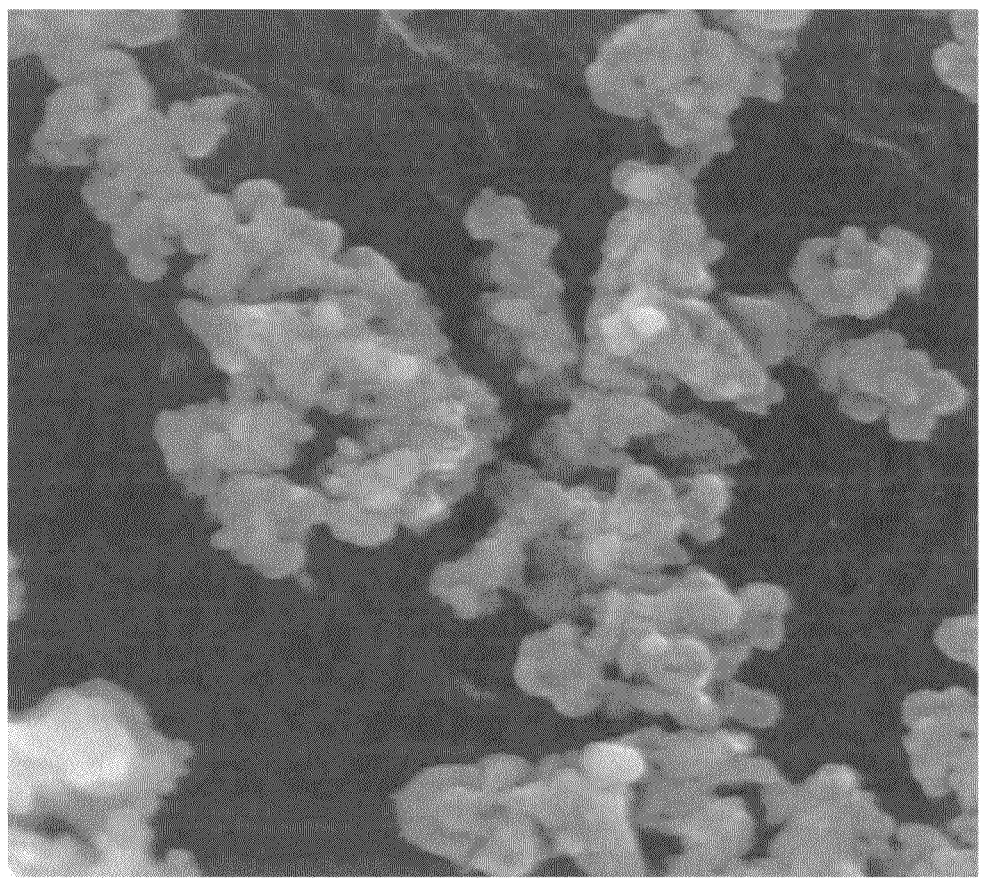
FIG. 6 is an SEM micrograph of a silica-coated silver colloid according to an exemplary embodiment of the present invention.
Figure 7:
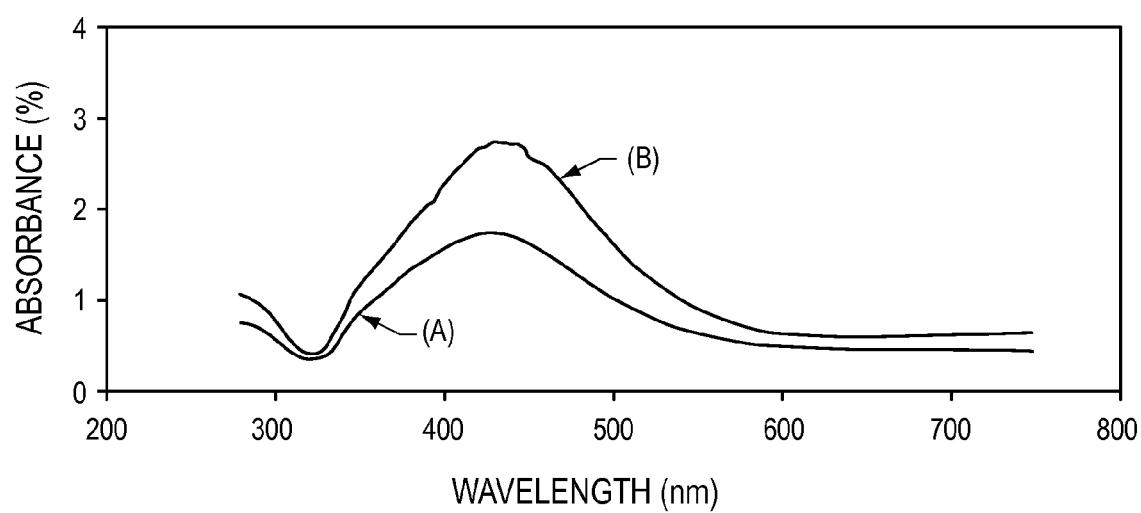
FIG. 7 is an absorption spectra of a silver colloid and a silica-coated silver colloid according to exemplary embodiments of the present invention.

FIG. 5 indicates the x-ray diffraction (XRD) pattern of the coating on glass. The XRD pattern indicates that the silica coated the silver particles completely and that the silica was in a non-crystalline state. The SEM micrograph of the silica-coated silver colloid is shown in FIG. 6. The absorption spectra, shown in FIG. 7, indicates that the absorption of the silver colloid of Example 1 (curve (A)) shifted to longer wavelengths as shown by the absorption spectra of Example 2 (curve (B)). The maximum absorption peak around 440 nm of the silica-coated silver colloid may be due to changes of the dielectric constant of the environment near the silver surface.

The silica-coated silver colloid of Example 2 was stable for at least 10 days.

It is noted that, as used in this specification and the appended claims, the singular forms "a," "an," and "the," include plural referents unless expressly and unequivocally limited to one referent, and vice versa. Thus, by way of example only, reference to "a coating" can refer to one or more coatings. As used herein, the term "include" and its grammatical variants are intended to be non-limiting, such that recitation of items in a list is not to the exclusion of other like items that can be substituted or added to the listed items.

It will be apparent to those skilled in the art that various modifications and variation can be made to the programs and methods of the present disclosure without departing from the scope its teachings. Other embodiments of the disclosure will be apparent to those skilled in the art from consideration of the specification and practice of the teachings disclosed herein. It is intended that the embodiments described in the specification be considered as exemplary only.

What is claimed is:

1. A method of preparing a silica-coated silver colloid, the method consisting essentially of:
    (a) heating a silver-containing solution;
    (b) combining the heated silver-containing solution with an acid solution;
    (c) cooling the combined solutions to form a silver colloid comprising silver particles;
    (d) adding aqueous ammonia and ethanol to the silver colloid; and
    (e) adding tetraethoxysilane to the silver colloid to form a silica-coated silver colloid comprising silica-coated silver particles,
    wherein said silica-coated silver colloid is stable for at least about 24 hours.

2. The method of claim 1, wherein said silver-containing solution comprises an aqueous solution of silver nitrate.

3. The method of claim 1, wherein said acid solution comprises at least one acid chosen from sodium citrate, citric acid, malic acid, and alkali-based acids.

4. The method of claim 1, wherein said silica-coated silver particles have a particle size less than about 300 nm.

5. The method of claim 1, wherein said silica-coated silver colloid is stable for at least about 10 days.

6. A method of forming an antimicrobial coating, the method consisting essentially of:
    (a) providing a substrate;
    (b) preparing a silver colloid by heating a silver-containing solution, combining the heated silver-containing solution with an acid solution, and cooling the combined solutions to form a silver colloid comprising silver particles;
    (c) adding aqueous ammonia and ethanol to the silver colloid; and
    (d) adding tetraethoxysilane to the silver colloid to form a silica-coated silver colloid comprising silica-coated silver particles;
    (e) coating the substrate with the silica coated silver particles; and
    (f) drying the coated substrate,
    wherein said silica-coated silver colloid is stable for at least about 24 hours.

7. The method of claim 6, wherein said silver particles have a particle size that ranges from about 10 nm to about 200 nm.

8. The method of claim 7, wherein said silver particles have a particle size that ranges from about 20 nm to about 150 nm.

9. The method of claim 6, wherein the silica-coated silver particles have a particle size less than about 300 nm.

10. The method of claim 6, wherein said substrate comprises a glass substrate.

* * * * *